United States Patent
Müller et al.

(10) Patent No.: US 9,403,754 B2
(45) Date of Patent: Aug. 2, 2016

(54) PROCESS FOR HYDROGENATING AROMATIC DI- AND POLYAMINES

(71) Applicant: Bayer MaterialScience AG, Leverkusen (DE)

(72) Inventors: Thomas E. Müller, Aachen (DE); Christoph Gürtler, Köln (DE); Reinhard Halpaap, Odenthal (DE); Christoph Thiebes, Köln (DE); Ewa Gebauer-Henke, Aachen (DE); Isabel U. Castro Cevallos, Aachen (DE); Walter Leitner, Aachen (DE)

(73) Assignee: Bayer MaterialScience AG (DE)

(*) Notice: Subject to any disclaimer, the term of this patent is extended or adjusted under 35 U.S.C. 154(b) by 0 days.

(21) Appl. No.: 14/614,013

(22) Filed: Feb. 4, 2015

(65) Prior Publication Data
US 2015/0218082 A1    Aug. 6, 2015

(30) Foreign Application Priority Data
Feb. 5, 2014 (EP) .................................. 14153936

(51) Int. Cl.
C07C 209/72 (2006.01)
B01J 23/46 (2006.01)

(52) U.S. Cl.
CPC .............. *C07C 209/72* (2013.01); *B01J 23/464* (2013.01); *C07C 2101/14* (2013.01); *Y02P 20/582* (2015.11)

(58) Field of Classification Search
CPC .............................. C07C 209/72; B01J 23/464
See application file for complete search history.

(56) References Cited

U.S. PATENT DOCUMENTS

| | | | | |
|---|---|---|---|---|
| 4,448,995 A | * | 5/1984 | Allen | 564/451 |
| 5,214,212 A | * | 5/1993 | Whitman | 564/451 |
| 5,360,934 A | * | 11/1994 | Vedage et al. | 564/451 |
| 5,516,935 A | | 5/1996 | Bischof et al. | |
| 6,075,167 A | | 6/2000 | Kim et al. | |
| 2010/0292510 A1 | | 11/2010 | Pfeffinger et al. | |
| 2012/0226017 A1 | * | 9/2012 | Pfeffinger et al. | 528/405 |

FOREIGN PATENT DOCUMENTS

| | | |
|---|---|---|
| EP | 0630882 A1 | 12/1994 |
| EP | 1078918 A1 | 2/2001 |

OTHER PUBLICATIONS

Kim et al., "Ru-catalyzed hydrogenation of aromatic diamines: The effect of alkali metal salts", J. Mol. Cat A: Chem. 132 (1998) 267-276.

* cited by examiner

*Primary Examiner* — Sudhakar Katakam
(74) *Attorney, Agent, or Firm* — Drinker Biddle & Reath LLP

(57) ABSTRACT

A catalytic process for hydrogenating aromatic di- and polyamines with the aid of a selected catalyst system is provided, which comprises a mixture of a first heterogeneous catalyst and a second heterogeneous catalyst and a nitro compound (nitrate and/or nitrite salt). The first and second heterogeneous catalyst each independently comprise a metal selected from the group consisting of Cr, Mo, W, Mn, Re, Fe, Ru, Os, Co, Rh, Ir, Ni, Pd and/or Pt and the metal selected for the second heterogeneous catalyst is different from the metal selected for the first heterogeneous catalyst. Hydrogenation of aromatic rings having two or more amino groups bound to the aromatic ring produces cycloaliphatic di- and polyamines, which are useful chemical intermediates, e.g., for further reaction with epoxides or isocyanates. The amino groups may also be converted to isocyanates via reaction with phosgene. The resulting cycloaliphatic di- and polyisocyanates may also be used as monomers for making polymers.

12 Claims, No Drawings

PROCESS FOR HYDROGENATING AROMATIC DI- AND POLYAMINES

This application claims the benefit of European Patent Application 14153936.1 filed Feb. 5, 2014, the entire disclosure of which is incorporated herein by reference.

FIELD OF THE INVENTION

The present invention relates to a catalytic process for hydrogenating aromatic amines with the aid of a selected catalyst system.

BACKGROUND OF THE INVENTION

Hydrogenation of aromatic rings having two or more amino groups bound to the aromatic ring produces amino-substituted hydrogenated rings, such as cycloaliphatic di- or polyamines, which are useful chemical intermediates, e.g., for further reaction with epoxides or isocyanates. The amino groups may also be converted to isocyanate groups e.g. via reaction with phosgene or through known phosgene free methods. The resulting cycloaliphatic di- or higher functional isocyanates may also be used as monomers for making polymers, in particular, polyurethanes.

Until now, many polyurethane materials are made based on aromatic di- and polyamines as starting materials. A disadvantage of using aromatic di- and polyamines is that the amines, the corresponding aromatic di- and polyisocyanates and the resulting products darken with time and gradually turn brown or black e.g. due to oxidation upon contact with air. Products derived from aliphatic and/or cycloaliphatic isocyanates behave differently and are known as "light stable" after conversion to polyisocyanates or polyurethanes. The stability of compounds derived from di- and polyamines may be improved by hydrogenating the aromatic ring to the corresponding cycloaliphatic di- and polyamines. Known heterogeneous hydrogenation catalysts, however, lack in sufficient activity for the core-hydrogenation of amino-substituted aromatic rings and lack in chemoselectivity towards primary amines. Frequently observed side reactions include the condensation of primary amino groups to secondary or tertiary amino groups and/or the hydrogenolytic cleavage of the C—N bond between the aromatic ring and the amino group.

Moreover, many applications of di- and polyamines, such as for making active ingredients in the pharmaceutical industry or use as a monomer for making polymers, require a high degree of stereomeric selectivity with regard to the position of the substituents relative to each other on the hydrogenated ring, such as the resulting cycloaliphatic ring. When incorporated into a polymer chain, e.g., by conversion to the corresponding diisocyanate and subsequent reaction with a diol, trans-1,4-diaminocyclohexane results in a polymer chain with linear connections, while cis-1,4-diaminocyclohexane results in a polymer chain with non-linear connections. Materials made from polymers with such linear or non-linear connections display different macroscopic properties, such as a different glass transition temperature. The properties of materials made from diastereomer mixtures of 1,4-diaminocyclohexanes vary in their properties with the content of the different diastereomers. Therefore, control of the ratio of the diastereomers is essential for controlling the properties of such materials. Diastereomers also may have different reactivities, so that compositions having a high proportion of one diastereomer can improve the uniformity of reaction rates when used in subsequent reactions, such as polyaddition or phosgenation reactions.

1,2-Diaminocyclohexanes with two amino groups attached to the same cycloaliphatic ring system in the 1,2-positions, as represented by formulas (I), which contain a high proportion of amino groups in cis position to each other, are advantageous for the reaction with phosgene. This is because the cis isomers are less prone than the trans isomers to form cyclic urea compounds, which are undesired by-products in the synthesis of isocyanates.

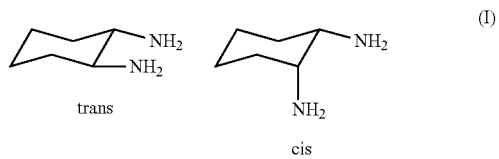 [SMILES: NC1CCCCC1N ; NC1CCCCC1N]

1,3-Diaminocyclohexanes with two amino groups attached to the same cycloaliphatic ring system in the 1,3-positions, as represented by formulas (II), which contain a high proportion of amino groups in trans position to each other are advantageous for the reaction with phosgene. This is because the trans isomers cannot form cyclic urea compounds, which are undesired by-products in the synthesis of isocyanates.

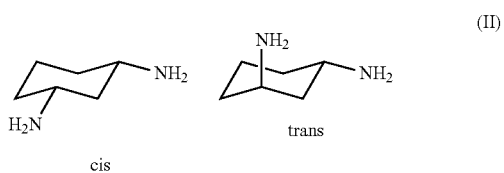 [SMILES: NC1CCCC(N)C1 ; NC1CCCC(N)C1]

1,4-Diaminocyclohexanes with the two amino groups attached to the same cycloaliphatic ring system in the 1,4-positions, as represented by formulas (III), which contain a high proportion of amino groups in trans position to each other, are advantageous for the reaction with phosgene. This is because the trans isomers cannot form cyclic urea compounds, which are undesired by-products in the synthesis of isocyanates.

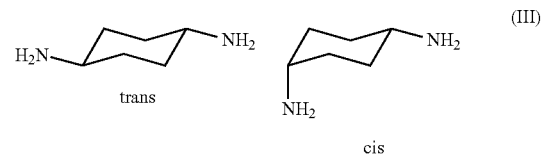 [SMILES: NC1CCC(N)CC1 ; NC1CCC(N)CC1]

Among the methyl substituted 2,4-diaminocyclohexane derivatives represented by formulas (IV) trans-cis-2,4-diamino-1-methyl-cyclohexane and cis-trans-2,4-diamino-1-methyl-cyclohexane, whereby cis and trans each refer to the position of the respective amino group relative to the methyl group, obtained by hydrogenating 2,4-diaminotoluene (2,4-TDA), are particularly advantageous for phosgenation, since these diastereomers do not form cyclic compounds, and trans-trans-2,4-diamino-1-methyl-cyclohexane, another diastereomer obtained by hydrogenating 2,4-TDA, is considered acceptable, since this diastereomer is less prone to form cyclic compounds, while cis-cis-2,4-diamino-1-methyl-cyclohexane is particularly prone to forming cyclic urea compounds during phosgenation.

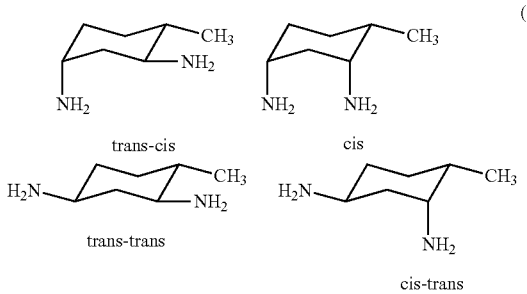

Analogously, among the methyl substituted 2,6-diaminocyclohexane derivative as represented by formulas (V), cis-trans-2,6-diamino-1-methyl-cyclohexane, obtained by hydrogenating 2,6-diaminotoluene (2,6-TDA), is particularly advantageous for phosgenation, since this diastereomer does not form cyclic compounds, and trans-trans-2,6-diamino-1-methyl-cyclohexane, another diastereomer obtained by hydrogenating 2,6-TDA, is considered acceptable, since this diastereomer is less prone to form cyclic compounds, while cis-cis-2,6-diamino-1-methyl-cyclohexane is particularly prone to forming cyclic urea compounds during phosgenation.

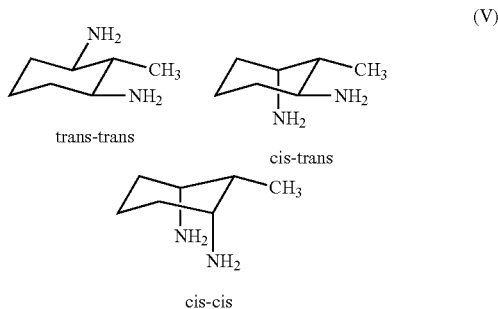

The phosgenation of such cycloaliphatic 1,2- or 1,3-diamines is known, see EP-B 1078918. Independent from ease of phosgenation, the preferred diastereomers are advantageous for the modification (oligomerisation) of the synthesized diisocyanates.

The use of conventional catalysts for the hydrogenation of 2,4-TDA or 2,6-TDA tends to provide diastereomer mixtures having a high proportion of undesired isomers, such as the cis-cis isomer.

An example of a hydrogenation of aromatic amines is given in EP 0 630 882 A1. Ring hydrogenation is effected by reacting the aromatic amine with $H_2$ in the presence of a catalyst comprising Rh on kappa-alumina. Also claimed is a process for hydrogenating crude methylene-dianiline (MDA) to produce 4,4'-methylene-dicyclohexylamine (PACM) in the presence of a 7:1 mixture of a Rh catalyst and a Ru catalyst, where at least the Rh catalyst is supported on kappa-alumina. The obtained product comprised 1 to 3% deaminated products and 13 to 19% secondary amines. It would be desirable to have access to catalytic systems having a lower rhodium content and displaying a higher reaction rate also for less reactive aromatic amines, as well as improved chemoselectivity with respect to the corresponding ring hydrogenated product.

An example of the use of additives in the hydrogenation of aromatic amines is given in Kim et al., J. Mol. Cat A: Chem. 132 (1998) 267-276. The influence of added alkali metal salts on the performance of ruthenium catalysts has been examined. It was found that the cations of the metal salts interact with the supporting material. $NaOCH(CH_3)_2$ was identified as the active species. The product obtained in the hydrogenation of methylene-dianiline (MDA) and 1,4-phenylenediamine comprised 2 to 99% of products with partially hydrogenated aromatic rings, 1 to 5% deaminated products, as well as 2 to 7% secondary amines. It would be desirable to have access to catalytic systems having an higher reaction rate also for less reactive aromatic amines, as well as improved chemoselectivity with respect to primary amino groups.

US 2010/292510 A1 relates to a process for preparing cycloaliphatic amines comprising performing hydrogenation of corresponding aromatic compounds with hydrogen-comprising gas at a temperature of from 30 to 280° C. and a pressure of 50-350 bar, in the presence of ruthenium catalysts, and from 1% by weight to 500% by weight, based on the catalyst (calculated as elemental ruthenium (Ru)), of suspended inorganic additives.

U.S. Pat. No. 5,214,212 teaches the addition of metal salts as promoters in a process for hydrogenating aromatic amines. According to the disclosure, the addition of promoters leads to an improvement in the reaction rate and to a reduction in by-product formation. To maintain high activity of the catalyst system in the hydrogenation process, a transition and/or lanthanide metal salt promoter is added to the reaction system in an effective amount to increase the hydrogenation rate, eliminate the induction period of the hydrogenation reaction, and decrease the amount of higher boiling by-products. By way of illustration, an effective amount of the transition or lanthanide metal salt promoter is in the range from about 0.1% to about 15% by weight based on the starting aromatic amine. The preferred range is from about 0.3% to about 10.0%. These metal salt promoters can be used alone or in combination with other additives. Counter-ions such as the sulfate and phosphate can be used because they do not have non-bonded electrons on the sulfur and phosphorus. respectively. Thus, ferrous and cerous sulfates (either as the anhydrous salt or as a hydrate) are illustrative. Other anions that satisfy these criteria such as carboxylates (e.g. acetates) can be used.

U.S. Pat. No. 4,448,995 teaches a process for the catalytic hydrogenation of di(4-aminophenyl)methane to a liquid di(4-aminocyclohexyl)methane containing from 15 to 40% by weight of the trans-trans isomer comprising hydrogenating di(4-aminophenyl)methane at a hydrogen pressure of at least 500 psi and at a temperature of from 100 to 300° C., in the presence of a ruthenium catalyst supported on an inert carrier, said catalyst being moderated with from 65 to 700% by weight, based on the weight of the ruthenium, of a compound selected from the group consisting of nitrates and sulfates of alkali metals and alkaline earth metals. According to one embodiment, the catalyst is moderated with a compound selected from the group consisting of lithium nitrate and magnesium nitrate.

U.S. Pat. No. 6,075,167 relates to a method of preparing cycloaliphatic diamines by hydrogenating an aromatic diamine in an organic solvent in the presence of a supported ruthenium catalyst, wherein a metal nitrite is used as a catalyst promoter. In one embodiment, the metal nitrite is selected from the group consisting of $Ba(NO_2)_2$, $NaNO_2$, $KNO_2$ and $AgNO_2$.

SUMMARY OF THE INVENTION

The present invention has as an object providing cycloaliphatic di- and polyamines in the hydrogenation of the corresponding aromatic di- and polyamines with a higher catalyst activity compared to the state of the art, in order to shorten the time required for the hydrogenation reaction. A high initial catalyst activity enables achievement of higher conversions, when the reaction is stopped at a certain reaction time characterised by a partial conversion of the aromatic di- and polyamine. Unconverted starting material is separated and recycled. This procedure provides a high space-time yield (optimal utilization of the reactor) as the hydrogenation reaction slows down proportionally, when high conversions are approached. Further, the process for hydrogenating aromatic di- and polyamines provides cycloaliphatic di- and polyamines with high chemoselectivity with respect to the ring hydrogenated product. Further, the cycloaliphatic di- and polyamines obtained are characterised by a sufficiently low content of ring-forming diastereomers, such as the cis-cis isomer in case of 2,6-TDA and/or 2,4-TDA hydrogenation.

According to the present invention, these and other objects are achieved by a process for hydrogenating aromatic amines comprising the steps of:
  reacting, in a reactor, at least one aromatic amine with hydrogen in the presence of a catalytic system, wherein the catalytic system comprises a mixture of a first heterogeneous catalyst and a second heterogeneous catalyst,
  wherein the first and second heterogeneous catalyst each independently comprises a metal selected from the group consisting of Cr, Mo, W, Mn, Re, Fe, Ru, Os, Co, Rh, Ir, Ni, Pd, Pt and combinations thereof, and the metal selected for the second heterogeneous catalyst is different from the metal selected for the first heterogeneous catalyst, and
  wherein the catalyst system further comprises a nitrate salt, a nitrite salt, or a combination thereof, and
  obtaining a reaction product from the reaction.

In one embodiment of the process according to the invention the aromatic amine is selected from the group consisting of o-, m-, and p-phenylenediamine, 2,3-diaminotoluene, 2,4-diaminotoluene, 2,6-diaminotoluene, 3,4-diaminotoluene, 2,3-diamino-p-xylene, 2,5-diamino-p-xylene, 2,6-diamino-p-xylene, N-methyl-o-phenylenediamine, N-ethyl-o-phenylenediamine, 4-methoxy-m-phenylenediamine, N-methyl-m-phenylenediamine, N-ethyl-m-phenylenediamine, N-isobutyl-p-phenylenediamine, N-isoamyl-p-phenylenediamine, N-cyclohexyl-p-phenylenediamine, N-benzyl-p-phenylenediamine, N-phenyl-p-phenylenediamine, N,N'-diethyl-p-phenylenediamine, N,N'-di(n-propyl)-p-phenylenediamine, N-methyl-N'-(n-propyl)-p-phenylenediamine, N-(n-butyl)-N'-benzyl-p-phenylenediamine, N,N'-dibenzyl-p-phenylenediamine, benzidine; N,N,N',N'-tetramethylbenzidine, 4,4'-oxydianiline, 4,4'-, 2,4'- and/or 2,2'-methylenedianiline, 4,4'-methylene-bis(N,N-dimethylaniline); 4,4'-methylene-bis(N-methylaniline), bis(3-methyl-4-aminophenyl)methane, 4,4'-ethylenedianiline, 2,4-diamino-N-phenylaniline, 2,4-bis(4-aminobenzyl)aniline, 1,2,4,5-tetraaminobenzene, bis(3,4-diaminophenyl)methane, and combinations thereof.

In another embodiment of the process according to the invention, the aromatic amine is 2,4-diaminotoluene and/or 2,6-diaminotoluene. If mixtures of 2,4-diaminotoluene and 2,6-diaminotoluene are used, the weight percentage of 2,6-diaminotoluene in the sum of the weights of 2,4-diaminotoluene and 2,6-diaminotoluene is preferably in the range up to 98%, more preferably in the range up to 80% and most preferably in the range up to 40%.

In another embodiment of the process according to the invention, the aromatic amine is 2,4-diaminotoluene and/or 2,6-diaminotoluene, and the reaction product comprises a mixture of 2,4-diamino-1-methyl-cyclohexane and 2,6-diamino-1-methyl-cyclohexane, wherein ≤45 mol % of the diamino-1-methyl-cyclohexanes reaction products are in the cis-cis-isomer configuration and ≤20 mol % of the diamino-1-methyl-cyclohexanes reaction products are in the trans-trans-isomer configuration.

In another embodiment of the process according to the invention, the metal of the first and/or second heterogeneous catalyst is on a support selected from the group consisting of alumina, silica, titania, ceria, carbon and combinations thereof.

In another embodiment of the process according to the invention, one metal of the first or second heterogeneous catalyst is ruthenium, rhodium, nickel or cobalt.

In another embodiment of the process according to the invention, the first heterogeneous catalyst is ruthenium on silica or ruthenium on alumina, and the second heterogeneous catalyst is rhodium on silica or rhodium on alumina, nickel on silica, nickel on alumina, cobalt on silica or cobalt on alumina.

In another embodiment of the process according to the invention, the first heterogeneous catalyst and the second heterogeneous catalyst are spatially separated from each other in the reactor.

In another embodiment of the process according to the invention, the metal of the first heterogeneous catalyst and the metal of the second heterogeneous catalyst are present as individual nanoparticles on a common support.

In another embodiment of the process according to the invention the process is conducted in the absence at least one of Pd and Pt.

In another embodiment of the process according to the invention, either the nitrate salt, the nitrite salt, or both, are selected as follows: the nitrate salt is selected from the group consisting of $LiNO_3$, $NaNO_3$, $KNO_3$, $NR'_4NO_3$, $PR'_4NO_3$ and combinations thereof, wherein R' is a C1 to C18 alkyl or aryl group and each R' may be different; and the nitrite salt is selected from the group of $LiNO_2$, $NaNO_2$, $KNO_2$, $NR'_4NO_2$, and $PR'_4NO_2$, wherein R' is a C1 to C18 alkyl or aryl group and each R' may be different.

In another embodiment of the process according to the invention the nitrate salt and/or nitrite salt is added into the reactor during the course of the reaction.

In another embodiment of the process according to the invention the reactor is a trickle bed reactor.

In another embodiment of the process according to the invention the reaction is carried out at a temperature in the range from ≥120° C. to ≤250° C.

In another embodiment of the process according to the invention the reaction is carried out in the presence of a solvent having ether or alcohol groups.

DETAILED DESCRIPTION OF THE INVENTION

The process according to this invention provides a means for hydrogenating compounds having aromatic rings substituted with two or more primary amino groups with a higher rate and higher selectivity to cycloaliphatic amines with two or more primary amino groups than those produced using state of the art catalysts or catalyst systems. The process according to this invention also provides a means for hydrogenating amines with two or more primary amino groups in meta or para position to each other to obtain diastereomer mixtures with a sufficient percentage of cis-configuration. When the starting material is selected, e.g., from 2,6-diaminotoluene and/or 2,4-diaminotoluene a sufficient percentage on a molar basis of the resulting diamino-1-methyl-cyclohexane compounds are in the cis-trans, trans-cis and trans-trans configuration to enable downstream processing, such as phosgenation.

Surprisingly, the inventors have found that the rate of the reaction and the chemoselectivity are improved by the use of catalyst mixtures in combination with the addition of a nitrate and/or nitrite salt, while a high diastereomer selectivity towards is maintained.

The cycloaliphatic primary polyamines made according to this invention are useful for further reaction with polyepoxides or polyisocyanates. The primary amino groups of the hydrogenated products may also be converted to isocyanates via reaction with phosgene or through phosgene free methods. The resulting cycloaliphatic isocyanates with two or more isocyanate groups may be used as monomers for making polymers, such as polyurethanes or modified polyisocyanates useful as crosslinkers to form polyurethanes and/or polyureas. The cycloaliphatic primary polyamines may also be used for making active ingredients in the pharmaceutical industry.

The process according to this invention uses aromatic amines or a mixture of two or more aromatic amines as a starting material. The aromatic amine in the context of this invention is a compound having at least one aromatic ring and at least two amino groups bound to the aromatic system. The two amino groups may be bound to the same aromatic ring or may be bound to two different aromatic rings. In a preferred embodiment, at least two amino groups are bound to the same aromatic ring. When the aromatic amine has more than one aromatic ring, the rings may be condensed or joined by at least two common ring members, a bond between a ring member of each aromatic ring or a divalent moiety. The divalent moiety preferably comprises C, O, S or N, more preferably from 1 to 6 C atoms. In a preferred embodiment, the divalent moiety is methylene.

At least two substituents, preferably up to four substituents, and even more preferably two substituents of an aromatic amine, are amino groups. The amino groups are preferably primary or secondary amino groups, and more preferably primary amino groups. Preferably, at least one amino group is in the 2-, or 4-position, more preferably at least one amino group is in the 2-position relative to a hydrocarbon group, preferably a methyl group, on at least one, preferably only one, aromatic ring. More preferably, amino groups are present in the 2- and the 4- or 6-position of at least one, preferably only one, aromatic ring.

In general, examples of aromatic amines include aminobenzenes with two amino groups attached to the same aromatic ring system as represented in formula (VI),

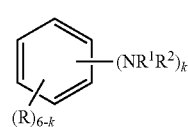

wherein
R is hydrogen, halogen, linear or branched C1-C12 alkyl, linear or branched C1-C12 alkoxy, linear or branched C1-C12 alkoxyalkyl,
$R^1$ and $R^2$ are independently hydrogen, or linear or branched C1-C12 alkyl and
k is an integer from 2 to 4.

Other examples for aromatic amines include aminonaphthalenes with at least two amino groups attached to the aromatic ring system as represented in formula (VII),

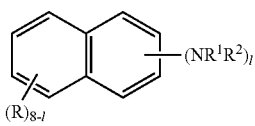

wherein
R is hydrogen, halogen, linear or branched C1-C12 alkyl, linear or branched C1-C12 alkoxy, linear or branched C1-C12 alkoxyalkyl,
$R^1$ and $R^2$ are independently hydrogen, or linear or branched C1-C12 alkyl, l is an integer from 2 to 4 and the substituents R and $NR^1R^2$ can be present at any position of the naphthalene ring.

Further examples include bridged polynuclear aromatic amines with two amino groups as represented in formula (VIII),

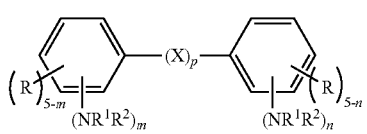

wherein
R is hydrogen, halogen, linear or branched C1-C12 alkyl, linear or branched C1-C12 alkoxy, linear or branched C1-C12 alkoxyalkyl,
$R^1$ and $R^2$ are independently hydrogen, or linear or branched C1-C12 alkyl,
X is linear or branched C1-C6 alkylene, O, S, $NR^3$ with $R^3$=linear or branched C1-C12 alkyl,
m and n is 0 or an integer from 1 to 3, and m+n≥2 and
p is 0 or 1.

The process according to this invention uses a catalyst system comprising two heterogeneous catalysts and a nitrate salt and/or a nitrite salt for conducting the hydrogenation of the aromatic amines.

Each heterogeneous catalyst comprises a metal selected from the group consisting of Cr, Mo, W, Mn, Re, Fe, Ru, Os, Co, Rh, Ir, Ni, Pd and/or Pt.

In the context of the present invention the term "heterogeneous catalyst" is meant to denote the combination of a catalytically active metal (Cr, Mo, W, Mn, Re, Fe, Ru, Os, Co, Rh, Ir, Ni, Pd and/or Pt) and a support.

A "mixture" of the two heterogeneous catalysts refers to two spatially separated heterogeneous catalysts comprising a first metal on a first support and a second metal on a second support. The term "mixture" may also be a physical mixture of a first metal on a first support and a second metal on a second support. The catalyst system according to the invention is not to be understood as being the result of a co-precipitation of two metals onto a shared support, as this would not meet the criterion of having two distinct catalysts. Likewise, the case of the first metal on a support doped with the second metal is also excluded.

The metal is preferably present on the support in the zero oxidation state, i.e., in elemental form. The corresponding oxide, hydroxide or other molecular compound may also be used, which is reduced to the metal prior to or during the hydrogenation of the aromatic amine. The metal is preferably present as nanoparticles, which have a volume-average particle size of ≥0.1 nm and ≤100 nm.

Preferably the metal comprises a single metal, whereby "single" includes technically unavoidable impurities. In an alternative embodiment, the metal comprises a main component of the above mentioned group and minor components of a second or more elements. The weight ratio of the main component to the minor component is preferably ≥80:≤20, more preferably ≥90:≤10 and most preferably ≥95:≤5.

The support is preferably a solid or gel material, which is preferably inert with respect to the aromatic amine and hydrogen under hydrogenation conditions. The support is preferably a particulate support. The particulate support may have a volume-average particle size of preferably ≥0.01 mm and ≤10 cm, more preferably ≥0.1 mm and ≤2 cm. Preferably, the support is a porous support.

The physical shape of the support may vary. The support particles may adopt the shape of a powder, pellets or extrudates. The surface area of the support is preferably ≥1 $m^2/g$ and ≤1000 $m^2/g$, more preferably ≥10 $m^2/g$ and ≤800 $m^2/g$ and most preferably ≥50 $m^2/g$ and ≤600 $m^2/g$. The surface area of the support can be determined using any method known to those of skill in the art. Suitable methods include the BET (Brunauer, Emmett & Teller) method using $N_2$ adsorption, such as described in DIN (Deutsches Institut fin Normung, e. V.) Standard 66131.

A wide range of support materials may be used. The support is preferably selected from the group comprising kappa, delta, gamma and theta alumina, silica, titania, zirconia, ceria, zeolites, such as ZSM-5, Beta, or mesoporous materials, such as SBA-15, polymer beads, such as beads of divinylbenzene-styrene-copolymer and/or carbon materials, such as active carbon or carbon nanotubes.

The metal may be bound chemically to the surface of the support, physisorbed on the surface of the support or encapsulated in pores of the support. The metal may also be encapsulated in the support and become accessible during the hydrogenation of the aromatic amines.

The weight ratio between the metal and the support is preferably ≥0.002 and ≤20, more preferably ≥0.005 and ≤5 and most preferably ≥0.01 and ≤0.1. Alternatively, the total metal surface area on the catalyst is preferably ≥0.01 $m^2/g$ and ≤50 $m^2/g$ of the catalyst, more preferably ≥0.05 $m^2/g$ and ≤10 $m^2/g$.

The catalyst system comprises at least two metals selected from the aforementioned group. Each metal is preferably independently combined with a support to form a heterogeneous catalyst prior to combining the heterogeneous catalyst with a heterogeneous catalyst comprising a different metal. When the support of a heterogeneous catalyst is a particulate support, each particle of the particulate support is preferably combined with only one metal selected from the above group of metals.

The catalyst system may comprise a first heterogeneous catalyst comprising a first metal selected from the above group combined with a first support and a second heterogeneous catalyst comprising a second metal selected from the above group, which is different from the first metal combined with a second support, wherein the chemical composition of the first support and the second support may be the same or different. The weight part of the second heterogeneous catalyst with respect to the entire catalyst system is preferred to be ≥0.1 weight-%, more preferred ≥1 weight-% and most preferred ≥5 weight-%.

The catalyst system may further comprise a third heterogeneous catalyst comprising a third metal selected from the above group, which is different from the first metal and the second metal combined with a third support, wherein the chemical composition of the third support may be the same or different from that of the first particulate support and the second support.

The catalyst system may further comprise a third heterogeneous catalyst comprising the first or second metal selected from the above group, which is combined with a third support, wherein the chemical composition of the third support is different from that of the first and the second support.

The catalyst system may also comprise additional heterogeneous catalysts analogous to the first, second and third heterogeneous catalyst.

In the foregoing embodiments, each support is preferably a particulate support. More preferably, each and every support is a particulate support.

The catalyst system further comprises an additive comprising a nitrate salt and/or a nitrite salt.

The reaction is preferably conducted under a pressure greater than atmospheric pressure. In one embodiment, the pressure is at least 20 bar (20 kPa), more preferably at least 50 bar (50 kPa), and even more preferably at least 80 bar (80 kPa).

Suitable reactors for the hydrogenation of the aromatic amine include a stirred tank reactor, a tubular reactor and a loop reactor. A particularly suitable reactor is a stirred tank reactor with gas entrainment, whereby the heat of reaction is preferably removed with an internal or external heat exchanger. Another particularly suitable reactor is a trickle bed reactor, whereby the flow direction of the hydrogen and the liquid phase are in the same direction upwards or downwards with respect to gravity (up-flow or down-flow), or in the opposite direction (counter-flow).

Particularly preferred is the combination of a trickle bed reactor with spatially separated first and second catalysts. Zones with the first catalyst may be adjacent to zones with the second catalyst (as seen in the flow direction of the reaction mixture) or there may be inert sections between the catalyst zones.

The hydrogenation of the aromatic amine can be performed in batch, semi-batch or continuous operation. In a preferred embodiment, the hydrogenation of the aromatic amine is performed in semi-batch operation, whereby the consumed hydrogen is replaced by feeding hydrogenation. In another preferred embodiment of the invention, the hydrogenation of the aromatic amine is performed in a continuous operation, whereby the aromatic amine and hydrogen are continuously fed to the reactor and the product mixture is continuously removed from the reactor.

The two heterogeneous catalysts may be present as a mixture or placed spatially separated in adjoined flow-through catalyst baskets or consecutive, alternating or nested catalyst beds.

In batch and semi-batch processes, the components of the catalyst system can be added to the reaction mixture separately or as a mixture. The components of the catalyst system can be added to the reaction mixture at the same time or at different times. In a preferred embodiment of the invention, the first heterogeneous catalyst and the second heterogeneous catalyst are placed spatially separated in adjoined flow-through catalyst baskets. The nitrate salt and/or nitrite salt may be part of the catalyst system charged into the reactor or may be charged separately into the reactor before, together with or subsequent to the catalyst. In a preferred embodiment of the invention, the heterogeneous catalyst is treated with the nitrate salt and/or nitrite salt and the combined catalyst system comprising heterogeneous catalyst and nitrate salt and/or nitrite salt is charged into the reactor.

In continuous processes, the aromatic amine and hydrogen are continuously fed to the reactor and the product mixture is continuously removed from the reactor. The at least two heterogeneous catalysts may be placed into the reactor as a mixture or separately in consecutive, alternating or nested beds. The nitrate salt and/or nitrite salt may be part of the heterogeneous catalyst placed into the reactor or added simultaneously with the amine, preferentially as a mixture with the amine. The amount of aromatic amine (in kg) intended for hydrogenation can be from ≥0.01 to ≤20, and more typically from ≥0.1 to ≤5 per 1 liter of catalyst per hour.

The reaction may be carried out in the presence of an inert solvent. The solvent is preferentially an organic solvent. In certain embodiments, the reaction is carried out in the presence of a solvent having ether or alcohol groups. Examples for such solvents include diethylether, dipropylether, dibutylether, methyl-butylether, tetrahydrofuran, 1,3-dioxane, 1,4-dioxane, or tetrahydro-2H-pyran, n-propanol, iso-propanol, n-butanol, iso-butanol and/or tert-butanol.

In another embodiment of the process according to the invention, the metal of the first heterogeneous catalyst and the metal of the second heterogeneous catalyst are present as individual nanoparticles on a common support.

Further aspects and embodiments of the present invention will be described below. They may be combined freely unless the context clearly indicates otherwise.

In one embodiment of the process according to the invention the aromatic amine is selected from the group consisting of o-, m-, and p-phenylenediamine, 2,3-diaminotoluene, 2,4-diaminotoluene, 2,6-diaminotoluene, 3,4-diaminotoluene, 2,3-diamino-p-xylene, 2,5-diamino-p-xylene, 2,6-diamino-p-xylene, N-methyl-o-phenylenediamine, N-ethyl-o-phenylenediamine, 4-methoxy-m-phenylenediamine, N-methyl-m-phenylenediamine, N-ethyl-m-phenylenediamine, N-isobutyl-p-phenylenediamine, N-isoamyl-p-phenylenediamine, N-cyclohexyl-p-phenylenediamine, N-benzyl-p-phenylenediamine, N-phenyl-p-phenylenediamine, N,N'-diethyl-p-phenylenediamine, N,N'-di(n-propyl)-p-phenylenediamine, N-methyl-N'-(n-propyl)-p-phenylenediamine, N-(n-butyl)-N'-benzyl-p-phenylenediamine, N,N'-dibenzyl-p-phenylenediamine, benzidine; N,N,N',N'-tetramethylbenzidine, 4,4'-oxydianiline, 4,4'-, 2,4'- and/or 2,2'-methylenedianiline, 4,4'-methylene-bis(N,N-dimethylaniline); 4,4'-methylene-bis(N-methylaniline), bis(3-methyl-4-aminophenyl)methane, 4,4'-ethylenedianiline, 2,4-diamino-N-phenylaniline, 2,4-bis(4-aminobenzyl)aniline, 1,2,4,5-tetraaminobenzene, and/or bis (3,4-diaminophenyl)methane.

In another embodiment of the process according to the invention, the aromatic amine is 2,4-diaminotoluene and/or 2,6-diaminotoluene. If mixtures are used the weight percentage of the 2,6-diaminotoluene in the sum of 2,4-diaminotoluene and 2,6-diaminotoluene is preferably in the range up to 98%, more preferably in the range up to 80% and most preferably in the range up to 40%.

In another embodiment of the process according to the invention, the aromatic amine is 2,4-diaminotoluene and/or 2,6-diaminotoluene, and the reaction product comprises a mixture of 2,4-diamino-1-methyl-cyclohexane and 2,6-diamino-1-methyl-cyclohexane wherein ≤45 mol % of the diamino-1-methyl-cyclohexanes are in the cis-cis-isomer configuration and ≤20 mol % of the diamino-1-methyl-cyclohexanes are in the trans-trans-isomer configuration.

In another embodiment of the process according to the invention the metal of the first and/or second heterogeneous catalyst is on a support selected from the group consisting of alumina, silica, titania, ceria and/or carbon.

In another embodiment of the process according to the invention one metal of the first or second heterogeneous catalyst is ruthenium, rhodium, nickel or cobalt.

In another embodiment of the process according to the invention the first heterogeneous catalyst is ruthenium on silica or ruthenium on alumina and the second heterogeneous catalyst is rhodium on silica or rhodium on alumina, nickel on silica, nickel on alumina, cobalt on silica or cobalt on alumina.

In another embodiment of the process according to the invention the first heterogeneous catalyst and the second heterogeneous catalyst are spatially separated from each other in the reactor. Using separate reaction zones may further improve the selectivity in certain reactions. An example would be to first hydrogenate in the presence of the first catalyst in a first reaction zone or reaction vessel and then transfer the product mixture to a second reaction zone or reaction vessel. Preferably a Ru-containing catalyst is the first catalyst. In an alternative embodiment, the reaction mixture several flows through several alternating catalyst zones. Placing the two heterogeneous catalysts separated from each other into the reaction can also facilitate recycling of the metal in the catalysts after their use.

In another embodiment of the process according to the invention the metal of the first heterogeneous catalyst and the metal of the second heterogeneous catalyst are present as individual nanoparticles on a common support. The nanoparticles of a metal have a volume-average particle size of preferably ≥0.1 nm and ≤100 nm. The two types of nanoparticles may be mixed and combined with the support.

In another embodiment of the process according to the invention the process is conducted in the absence of Pd and/or Pt.

In another embodiment of the process according to the invention the nitrate salt is selected from the group of $LiNO_3$, $NaNO_3$, $KNO_3$, $NR'_4NO_3$, and/or $PR'_4NO_3$, wherein R' is a C1 to C18 alkyl or aryl group and each R' may be different and/or the nitrite salt is selected from the group of $LiNO_2$, $NaNO_2$, $KNO_2$, $NR'_4NO_2$, $PR'_4NO_2$, wherein R' has the meaning mentioned above.

Without being limited to a theory, nitrate salts are reduced in the presence of hydrogen and heterogeneous catalysts to the corresponding nitrite salts, as described, e.g., in Barrabés et al., Appl. Catal. B: Environment. 62 (2006) 77-85.

In another embodiment of the process according to the invention the nitrate salt and/or nitrite salt is added into the reactor during the course of the reaction.

In another embodiment of the process according to the invention the reactor is a trickle bed reactor. Particularly preferred is the combination of a trickle bed reactor with spatially separated first and second catalysts. Zones with the first catalyst may be adjacent to zones with the second catalyst (as seen in the flow direction of the reaction mixture) or there may be inert sections between the catalyst zones.

In another embodiment of the process according to the invention the reaction is carried out at a temperature in the range from ≥120° C. to ≤250° C. Preferred reaction temperatures are ≥130° C. to ≤200° C., more preferred ≥140° C. to ≤180° C.

In another embodiment of the process according to the invention the reaction is carried out in the presence of a solvent having ether or alcohol groups. Examples for such solvents include diethylether, dipropylether, dibutylether, methyl-butylether, tetrahydrofuran, 1,3-dioxane, 1,4-dioxane, or tetrahydro-2H-pyran, n-propanol, iso-propanol, n-butanol, iso-butanol and/or tert-butanol.

A further aspect of the present invention is the use of a catalytic system for hydrogenating aromatic amines, wherein the catalytic system comprises a mixture of a first heterogeneous catalyst and a second heterogeneous catalyst and wherein the first and second heterogeneous catalyst each independently comprises a metal selected from the group consisting of Cr, Mo, W, Mn, Re, Fe, Ru, Os, Co, Rh, Ir, Ni, Pd and/or Pt and the metal selected for the second heterogeneous catalyst is different from the metal selected for the first heterogeneous catalyst. The catalyst system further comprises a nitrate salt and/or a nitrite salt. Likewise, all other aspects and embodiments of the catalyst system discussed above with respect to the process according to the invention may be applied to the use according to the invention. For reasons of brevity they are not repeated here.

The invention is further illustrated by way of the following examples, which are not intended to limit the overall scope of this invention.

EXAMPLES

The abbreviations used in the following examples are defined below:

| Designation | Definition |
| --- | --- |
| Ru1 | 5 wt. % Ru on $Al_2O_3$ from BASF (product no. 57497196) |
| Ru2 | 5 wt. % Ru on $Al_2O_3$ from Johnson Matthey Co. (product no. M11185) |
| Rh1 | 5 wt. % Rh on $Al_2O_3$ from Johnson Matthey Co. (product no. M11196) |
| Ni1 | 46.6 wt. % Ni on $SiO_2$ from Johnson Matthey Co. (product no. 0812/2011) |
| 2,4-TDA | 2,4-Toluenediamine (98%) |
| 2,6-TDA | 2,6-Toluenediamine (97%) |

Test Protocol

If not stated otherwise, the starting material, namely a mixture of 0.64 g 2,4-TDA and 0.16 g 2,6-TDA in 90 ml tetrahydrofuran (THF), together with the catalyst system specified in the tables below, were charged into a pressurizable stainless steel autoclave vessel having a volume of 160 ml. The mixture was stirred using a gas entrainment stirrer at a rate of 600 revolutions per minute and heated to the temperature, T When the catalysts Ru1, Ni1 or mixtures of both catalysts were used, the temperature T was set to 160° C. When the catalysts Ru2, Rh1 or mixtures of both catalysts were used, the temperature T was set to 140° C. The autoclave vessel was then pressurised with hydrogen to 100 bar (100 kPa). The mixture was stirred continuously for a total of 450 minutes, while holding the temperature constant at the specified temperature and the pressure in the autoclave vessel constant at 100 bar (100 kPa) by feeding further hydrogen from a hydrogen holding tank having a known volume and pressure into the mixture to compensate for hydrogen used by the reaction. At the end of the 450 minute time period allotted for the reaction, the feeding of hydrogen gas was discontinued, the autoclave vessel cooled to 25° C. and the pressure within the autoclave vessel carefully released down to atmospheric pressure. The liquid product mixture was removed from the vessel, filtered and subjected to gas chromatography to determine the composition of the product mixture.

The rate of hydrogen consumption per minute was calculated from the drop in pressure in the hydrogen holding tank. The pressure drop was recalculated to the amount of hydrogen consumed. The data for the amount of hydrogen consumed as a function of time were fitted with equation (IX):

$$n_{H2}(t) = a\left(1 - \frac{1}{1+b \times t}\right) + (c \times t), \quad (IX)$$

where $n_{H2}(t)$ is the amount of hydrogen consumed with time, t is the time and a, b and c are real numbers used as fit parameters, which were varied until the least squares difference between the measured and the fitted data was minimal.

The initial reaction rate at time zero was calculated according to equation (X) by extrapolation of data collected for the rate of hydrogen consumption backward in time to time equals zero:

$$\text{Initial rate} = \frac{ab+c}{m(cat)}, \quad (X)$$

where a, b and c have the above mentioned meaning and m(cat) is the mass of the heterogeneous catalyst employed.

The relative amounts of remaining 2,4-TDA and 2,6-TDA, the formed primary amines thereby distinguishing the ortho and para ring-position isomers and the relative amounts of cis and trans isomers as well as deaminated monoamines and small amounts of binuclear secondary amines were determined by gas chromatography using a Hewlett Packard Model HP 6890 gas chromatography apparatus. The column used in gas chromatography was CP-Sil-PONA-CB (silica) with a length of 50 m and inner diameter of 0.21 mm. The carrier gas was helium with a constant flow of 1.5 ml/min. The injector temperature was set at 250° C. and the detector temperature was set at 300° C. For each sample, the gas chromatography temperature program was set to hold the column at a temperature of 110° C. for 20 minutes, after which the temperature of the column was ramped to a temperature of 250° C. at a rate of 10° C. per minute and then maintained at 250° C. for 10 minutes. The resulting areas under the peaks of the chromatograms were converted into mass fractions in wt % and the conversions were calculated according to equation (XI) in the case of TDA being the substrate and equation (XII) in the case of MDA being the substrate to be hydrogenated.

$$\text{Conversion} = \left(1 - \frac{c_{TDA}(t)}{\sum c_i}\right), \quad (XI)$$

where $c_{TDA}(t)$ is the concentration of TDA at the end of the experiment and $\Sigma c_i$ is the sum of the concentrations of TDA and all detected products.

$$\text{Conversion} = \left(1 - \frac{c_{MDA}(t)}{\sum c_k}\right), \quad (XII)$$

where $c_{MDA}(t)$ is the concentration of MDA at the end of the experiment and $\Sigma c_i$ is the sum of the concentrations of MDA and all detected products.

The chemoselectivity to ring hydrogenated diamines was calculated according to equation (XIII) in the case of TDA being the substrate and equation (XIV) in the case of MDA being the substrate to be hydrogenated.

$$\text{Chemoselectivity} = \left( \frac{c_{Diamino\text{-}methyl\text{-}cyclohexane}}{\Sigma c_k} \right) \times 100\%, \quad (XIII)$$

where $c_{Diamino\text{-}methyl\text{-}cyclohexane}$ is the sum of the concentration of all 2,4-diamino-1-methyl-cyclohexane and 2,6-diamino-1-methyl-cyclohexane isomers and $\Sigma c_k$ is the sum of the concentrations of all detected products.

$$\text{Chemoselectivity} = \left( \frac{c_{4,4'\text{-}Methylenedicyclohexanamine}}{\Sigma c_l} \right) \times 100\%, \quad (XIV)$$

where $c_{4,4'\text{-}methylenedicyclohexanamine}$ is the sum of the concentration of all 4,4'-methylenedicyclohexanamine isomers and $\Sigma c_l$ is the sum of the concentrations of all detected products The isomer content was calculated according to equation (XV)

$$\text{Isomer content} = \frac{c_{Isomer}}{c_{Diamino\text{-}methyl\text{-}cyclohexane}}, \quad (XV)$$

Where $c_{Isomer}$ is the diamino-methyl-cyclohexane isomer for which the isomer content is calculated.

The hydrogenation products of 2,4-TDA and 2,6-TDA are compositions comprising a mixture of diastereomers. The designations cis and trans refer to the positions of the respective amino groups relative to the position of the methyl group in the hydrogenated product. When 2,4-diamino-1-methyl-cyclohexane is made from 2,4-TDA, the first designation cis or trans refers to the position of the amino group in the ortho-position and the second designation cis or trans refers to the position of the amino group in the para-position, each relative to the methyl group. When 2,6-diamino-1-methyl-cyclohexane is made from 2,6-TDA, cis and trans refers to the position of the two amino groups in the ortho-position relative to the methyl group.

The following table summarizes the diastereomer permutations available for the 2,4-diamino and 2,6-diamino ring-position isomers and their retention times measured by gas chromatography as described above.

| Product | ortho-Position | para-Position | Retention Time |
|---|---|---|---|
| 2,4-Diamino-1-methyl-cyclohexane | trans | cis | 14.14 minutes |
| | cis | trans | 14.51 minutes |
| | trans | trans | 13.56 minutes |
| | cis | cis | 15.58 minutes |
| 2,6-Diamino-1-methyl-cyclohexane | trans-trans | — | 13.95 minutes |
| | cis-trans | — | 14.81 minutes |
| | cis-cis | — | 16.31 minutes |

In the following examples, the hydrogenation of aromatic di- and polyamines was conducted in accordance with the above test protocol using the catalyst systems specified below. The results obtained are reported in the following tables.

Example 1

Hydrogenation of a Mixture of 2,4-TDA and 2,6-TDA Using a Mixture of Ruthenium Catalyst Ru1 and Nickel Catalyst Ni1 in the Presence of a Nitro Compound Table 1A below shows data obtained for Example 1a according to this invention and Comparative Examples 1b* to 1d* by conducting the hydrogenation according to the above test protocol. Hydrogenation Example 1a was conducted with a combination of Ru1 and Ni1 as the heterogeneous catalysts and $NaNO_2$ as the nitro compound. The hydrogenations in Comparative Examples 1b* and 1c* were conducted in the same way as in Example 1a, except that the parent catalysts were used as the sole source of catalytic material. The hydrogenation in Comparative Example 1d* was conducted in the same way as in Example 1a, except that $NaNO_2$ was absent.

TABLE 1A

COMPARISON OF INITIAL REACTION RATES, CONVERSIONS AND CHEMOSELECTIVITIES FOR CATALYST SYSTEMS ACCORDING TO THE INVENTION RELATIVE TO COMPARATIVE CATALYST SYSTEMS

| Example | Ru1 grams | Ni1 grams | $NaNO_2$ grams | Initial Rate $mol_{H_2}/min/g_{cat}$ | Conversion percent | Selectivity percent |
|---|---|---|---|---|---|---|
| 1a | 0.24 | 0.002 | 0.01 | 0.0038 | 99.6 | 93.3 |
| 1b* | 0.24 | — | 0.01 | 0.0003 | 99.6 | 93.2 |
| 1c* | — | 0.024 | 0.01 | n.a. | 3.3 | 19.5 |
| 1d* | 0.24 | 0.002 | 0 | 0.0004 | 100 | 89.0 | n.a. = not applicable as an initial rate could not be calculated due to the low conversion The data in Table 1A show that the use of a catalyst mixture in combination with $NaNO_2$ according to this invention, results in an increase in the initial reaction rate relative to Comparative Example 1b*, in which the parent ruthenium catalyst was used as the sole source of catalytic metal. Also the chemoselectivity is improved, while maintaining the high conversion relative to Comparative Example 1b*. Hardly any conversion was obtained in Comparative Example 1c*, in which the parent nickel catalyst was used as the sole source of catalytic metal.

The data in Table 1A show that the addition of $NaNO_2$ according to this invention, results in an increase in the initial reaction rate relative to Comparative Example 1d*, in which $NaNO_2$ was absent. Also the chemoselectivity is improved in the presence of $NaNO_2$ relative to Comparative Example 1d*, in which $NaNO_2$ was absent. The desired high conversion is maintained in the presence of a nitro-additive relative to Comparative Example 1d*.

Table 1B shows the effect of $NaNO_2$ on diastereomer selectivity for Example 1a according to this invention relative to Comparative Examples 1b* to 1d*.

TABLE 1B

COMPARISON OF CIS AND TRANS ISOMER CONTENT
OF REACTION PRODUCTS MADE USING CATALYST
SYSTEMS ACCORDING TO THE INVENTION RELATIVE
TO COMPARATIVE CATALYST SYSTEMS

| Reaction Product | ortho-Position | para-Position | Ex. 1a % | Compar. Ex. 1b* % | Compar. Ex. 1c* % | Compar. Ex. 1d* % |
|---|---|---|---|---|---|---|
| 2,4-Diamino-1-methyl-cyclo-hexane | trans | cis | 12 | 23 | 11 | 18 |
| | cis | trans | 23 | 13 | 12 | 13 |
| | trans | trans | 8 | 27 | 25 | 29 |
| | cis | cis | 41 | 20 | 34 | 24 |
| 2,6-Diamino-1-methyl-cyclo-hexane | trans-trans | — | 1 | 3 | 2 | 2 |
| | cis-trans | — | 6 | 9 | 7 | 8 |
| | cis-cis | — | 9 | 5 | 8 | 6 |

As can be seen from the data presented in Table 1B, the desired high proportion of the trans-cis, cis-trans and trans-trans 2,4-diamino-1-methyl-cyclohexane and the trans-trans and cis-trans 2,6-diamino-1-methyl-cyclohexane isomers in the reaction product is maintained in the presence of a mixture of heterogeneous catalysts in the presence of a nitro-additive relative to Comparative Example 1b* to 1c*. Likewise, the desired high proportion of the trans-cis, cis-trans and trans-trans 2,4-diamino-1-methyl-cyclohexane and the trans-trans and cis-trans 2,6-diamino-1-methyl-cyclohexane isomers in the reaction product is maintained in the presence of a nitro-additive relative to Comparative Example 1d*.

Example 2

Hydrogenation of a Mixture of 2,4-TDA and 2,6-TDA Using a Mixture of Ruthenium Catalyst Ru2 and Rhodium Catalyst Rh1 in the Presence of an Additive Table 2 below shows data obtained for Example 2a according to this invention and Comparative Example 2b* to 2d* by conducting the hydrogenation according to the above test protocol. Hydrogenation Example 2 was conducted using a combination of Ru2 (0.23 g) and Rh1 (0.027 g) as the heterogeneous catalysts and $NaNO_2$ as the nitro compound. The hydrogenations in Comparative Examples 2b* and 2c* were conducted in the same way as in Example 2a, except that the parent catalysts were used as the sole source of catalytic material. The hydrogenation in Comparative Example 2d* was conducted in the same way as in Example 2a, except that $NaNO_2$ was absent.

TABLE 2A

COMPARISON OF INITIAL REACTION RATES, CONVERSIONS
AND CHEMOSELECTIVITIES FOR CATALYST SYSTEMS
ACCORDING TO THE INVENTION RELATIVE TO
COMPARATIVE CATALYST SYSTEMS

| Example | Ru2 grams | Rh1 grams | $NaNO_2$ grams | Initial Rate $mol_{H_2}$/min/$g_{cat}$ | Conversion percent | Selectivity percent |
|---|---|---|---|---|---|---|
| 2a | 0.24 | 0.027 | 0.01 | 0.0052 | 97.7 | 90.4 |
| 2b* | 0.27 | 0 | 0.01 | 0.0017 | 52.9 | 89.5 |
| 2c* | 0 | 0.27 | 0.01 | 0.0078 | 98.3 | 78.9 |
| 2d* | 0.24 | 0.027 | 0 | 0.0033 | 99.1 | 88.3 |

The data in Table 2A show that the use of a catalyst mixture in combination with $NaNO_2$ according to this invention, results in an increase in the initial reaction rate and chemoselectivity relative to Comparative Example 2b*, in which the parent ruthenium catalyst was used as the sole source of catalytic metal. In the case of Comparative Examples 2c*, in which the parent rhodium catalyst was used as the sole source of catalytic metal, the chemoselectivity was unacceptably low. The use of a catalyst mixture according to Example 2a further allows to reduce the amount of rhodium catalyst necessary for the hydrogenation reaction by a factor of 10.

The data in Table 2A show that the addition of $NaNO_2$ according to this invention, results in an increase in the initial reaction rate relative to Comparative Example 2d*, in which $NaNO_2$ was absent. Also the chemoselectivity is improved in the presence of $NaNO_2$ relative to Comparative Example 2d*, in which $NaNO_2$ was absent. The desired high conversion is maintained in the presence of a nitro-additive relative to Comparative Example 2d*.

Table 2B shows the effect of $NaNO_2$ and the usage of a mixture of two heterogeneous catalysts on diastereomer selectivity for Example 2a according to this invention relative to Comparative Examples 2b* and 2c*, where the parent catalysts were used as the sole source of catalytic material and Comparative Example 2d*, in which $NaNO_2$ was absent.

TABLE 2B

COMPARISON OF CIS AND TRANS ISOMER CONTENT
OF REACTION PRODUCTS MADE USING CATALYST
SYSTEMS ACCORDING TO THE INVENTION RELATIVE
TO COMPARATIVE CATALYST SYSTEMS

| Reaction Product | Ortho-Position | Para-Position | Ex. 2a % | Compar. Ex. 2b* % | Compar. Ex. 2c* % | Compar. Ex. 2d* % |
|---|---|---|---|---|---|---|
| 2,4-diamino-1-methyl-cyclo-hexane | trans | cis | 16 | 3 | 18 | 14 |
| | cis | trans | 18 | 9 | 30 | 18 |
| | trans | trans | 20 | 24 | 22 | 21 |
| | cis | cis | 32 | 43 | 21 | 33 |
| 2,6-diamino-1-methyl-cyclo-hexane | trans-trans | — | 2 | 2 | 1 | 2 |
| | cis-trans | — | 6 | 9 | 5 | 6 |
| | cis-cis | — | 6 | 10 | 3 | 6 |

As can be seen from the data presented in Table 2B, the desired high proportion of the trans-cis, cis-trans and trans-trans 2,4-diamino-1-methyl-cyclohexane and the trans-trans and cis-trans 2,6-diamino-1-methyl-cyclohexane isomers in the reaction product is maintained in the presence of a mixture of heterogeneous catalysts in the presence of a nitro-additive relative to Comparative Example 2b* to 2c*. Likewise, the desired high proportion of the trans-cis, cis-trans and trans-trans 2,4-diamino-1-methyl-cyclohexane and the trans-trans and cis-trans 2,6-diamino-1-methyl-cyclohexane isomers in the reaction product is maintained in the presence of a nitro-additive relative to Comparative Example 2d*.

Example 3

Hydrogenation of a Mixture of 2,4-TDA and 2,6-TDA at Higher Substrate Concentrations by Using Different Catalysts in the Presence of an Additive Table 3 below shows data obtained for Examples 3a to 3b according to this invention by conducting the hydrogenation using different catalysts as the heterogeneous catalysts according to the above test protocol, but using 16 g of 2,4-

TDA and 4 g of 2,6-TDA. Hydrogenation Examples 3a to 3b were conducted with catalyst systems comprising, in addition to the heterogeneous catalysts, $NaNO_2$.

TABLE 3

COMPARISON OF INITIAL REACTION RATES, CONVERSIONS AND CHEMOSELECTIVITIES FOR CATALYST SYSTEMS ACCORDING TO THE INVENTION AT A HIGHER SUBSTRATE CONCENTRATION

| Example | $V_{THF}$ mL | Catalyst System | Initial Rate $molH_2/min/g_{cat}$ | Conversion percent | Selectivity percent |
|---|---|---|---|---|---|
| 3a | 70 | 4.50 g Ru1<br>0.045 g Ni1<br>0.281 g $NaNO_2$ | 0.0009 | 96.9 | 92.2 |
| 3b | 70 | 4.13 g Ru2<br>0.504 g Rh1<br>0.188 g $NaNO_2$ | 0.0042 | 88.8 | 91.4 |

The data in Table 3 show that also at high concentrations of TDA high initial reaction rates, chemoselectivities and conversions are obtained with catalyst systems according to this invention.

Example 4

Hydrogenation of a Mixture of 2,4-TDA and 2,6-TDA Using a Mixture of Ruthenium Catalyst Ru1 and Nickel Catalyst Ni1 in the Presence of a Nitrite Salt at Higher Hydrogen Pressures Table 4 below shows data obtained for Examples 4a to 4c according to this invention by conducting the hydrogenation using a combination of ruthenium catalyst Ru1 (0.30 g) and nickel catalyst Ni1 (0.002 g) as the heterogeneous catalysts according to the above test protocol, but using 0.8 g of 2,4-TDA and 0.2 g of 2,6-TDA and varying the hydrogen pressure. Hydrogenation Examples 4a to 4b were conducted with catalyst systems comprising, in addition to the heterogeneous catalysts, $NaNO_2$ (0.01 g).

TABLE 4

COMPARISON OF INITIAL REACTION RATES, CONVERSIONS AND CHEMOSELECTIVITIES FOR CATALYST SYSTEMS ACCORDING TO THE INVENTION APPLYING HIGHER HYDROGEN PRESSURES

| Example | Pressure bar | Conversion percent | Selectivity percent |
|---|---|---|---|
| 4a | 110 | 98.7 | 93.0 |
| 4b | 120 | 99.4 | 93.9 |
| 4c | 140 | 99.8 | 94.3 |

The data in Table 4 show that also at higher hydrogen pressures the catalyst systems according to the invention provide the desired high conversions and chemoselectivities.

Example 5

Hydrogenation of a Mixture of 2,4-TDA and 2,6-TDA Using a Mixture of Ruthenium Catalyst Ru2 and Rhodium Catalyst Rh1 in the Presence of a Nitrite Salt at Higher Hydrogen Pressures Table 5 below shows data obtained for Examples 5a to 5c according to this invention by conducting the hydrogenation using a combination of ruthenium catalyst Ru2 (0.29 g) and rhodium catalyst Rh1 (0.034 g), but using 0.8 g of 2,4-TDA and 0.2 g of 2,6-TDA and varying the hydrogen pressure. Hydrogenation Examples 5a to 5c were conducted with catalyst systems comprising, in addition to the heterogeneous catalysts, $NaNO_2$ (0.01 g).

TABLE 5

COMPARISON OF INITIAL REACTION RATES, CONVERSIONS AND SELECTIVITY FOR CATALYST SYSTEMS ACCORDING TO THE INVENTION APPLYING HIGHER HYDROGEN PRESSURES

| Example | Pressure bar | Conversion percent | Selectivity percent |
|---|---|---|---|
| 5a | 120 | 96.9 | 90.5 |
| 5b | 130 | 98.3 | 89.7 |
| 5c | 140 | 95.8 | 89.4 |

The data in Table 5 show that also at higher hydrogen pressures the catalyst systems according to the invention provide the desired high conversions and chemoselectivities.

Example 6

Hydrogenation of 4,4'-Methylene Dianiline Using Different Catalytic Systems in the Presence of a Nitrite Salt Table 6 below shows data obtained for Examples 6a to 6d according to this invention by conducting the hydrogenation using different catalysts as the heterogeneous catalysts according to the above test protocol, but using 2 g of 4,4'-methylene dianiline instead of a mixture of 2,4- and 2,6-TDA. Hydrogenation Examples 6a to 6d were conducted with catalyst systems comprising, in addition to the heterogeneous catalysts, nitro-additives.

TABLE 6

COMPARISON OF INITIAL REACTION RATES, CONVERSIONS AND CHEMOSELECTIVITIES FOR CATALYST SYSTEMS ACCORDING TO THE INVENTION IN THE HYDROGENATION OF 4,4'-METHYLENE DIANILINE

| Example | Catalyst System | Initial Rate $mol_{H_2}/min/g_{cat}$ | Conversion percent | Selectivity percent |
|---|---|---|---|---|
| 6a | 0.36 g Ru1<br>0.003 g Ni1<br>0.011 g $NaNO_2$ | 0.0152 | 100 | 100 |
| 6b | 0.36 g Ru2<br>0.044 g Rh1<br>0.011 g $NaNO_2$ | 0.0077 | 100 | 100 |
| 6c | 0.36 g Ru1<br>0.003 g Ni1<br>0.011 g $KNO_2$ | 0.0062 | 99.6 | 99.4 |
| 6d | 0.36 g Ru2<br>0.044 g Rh1<br>0.011 g $KNO_2$ | 0.0025 | 100 | 97.4 |

The data in Table 6 show that the catalyst systems according to this invention are also applicable to the hydrogenation of 4,4'-methylene dianiline.

The present invention may be embodied in other specific forms without departing from the spirit or essential attributes thereof and, accordingly, reference should be made to the appended claims, rather than to the foregoing specification, as indicating the scope of the invention.

The invention claimed is:

1. A process for hydrogenating aromatic amines comprising the steps of:
reacting, in a reactor, a mixture of 2,4-diaminotoluene and 2,6-diaminotoluene with hydrogen in the presence of a catalytic system,
wherein the catalytic system comprises a mixture of a first heterogeneous catalyst comprising Ru and a second heterogeneous catalyst comprising Rh,
wherein the catalytic system further comprises a nitrate salt, a nitrite salt or a combination thereof, and
obtaining from the reaction a reaction product comprising a mixture of 2,4-diamino-1-methyl-cyclohexane and 2,6-diamino-1-methyl-cyclohexane, wherein ≤45 mol % of said diamino-1-methyl-cyclohexane reaction products are in the cis-cis-isomer configuration and ≤22 mol % of said diamino-1-methyl-cyclohexane reaction products are in the trans-trans-isomer configuration,
wherein the initial rate of the reaction is ≥0.0052 mol $H_2$/min/g of the catalytic system.

2. The process according to claim 1, wherein ≤20 mol % of said diamino-1-methyl-cyclohexane reaction products are in the trans-trans-isomer configuration.

3. The process according to claim 1, wherein the metal of the first and/or second heterogeneous catalyst is on a support selected from the group consisting of alumina, silica, titania, ceria, carbon, and combination thereof.

4. The process according to claim 1, wherein the first heterogeneous catalyst is comprised of ruthenium on silica or ruthenium on alumina and the second heterogeneous catalyst is comprised of rhodium on silica or rhodium on alumina.

5. The process according to claim 1, wherein the first heterogeneous catalyst and the second heterogeneous catalyst are spatially separated from each other in the reactor.

6. The process according to claim 1, wherein the metal of the first heterogeneous catalyst and the metal of the second heterogeneous catalyst are present as individual nanoparticles on a common support.

7. The process according to claim 1, wherein the process is conducted in the absence of at least one of Pd and Pt.

8. The process according to claim 1, wherein either the nitrate salt, the nitrite salt, or both, are selected as follows:
the nitrate salt is selected from the group consisting of $LiNO_3$, $NaNO_3$, $KNO_3$, $NR'_4NO_3$, $PR'_4NO_3$, and combinations thereof, wherein R' is a C1 to C18 alkyl or aryl group and each R' may be different,
and
the nitrite salt is selected from the group of $LiNO_2$, $NaNO_2$, $KNO_2$, $NR'_4NO_2$, $PR'_4NO_2$, wherein R' is a C1 to C18 alkyl or aryl group and each R' may be different.

9. The process according to claim 8, wherein the nitrate salt and/or nitrite salt is added into the reactor during the course of the reaction.

10. The process according to claim 1, wherein the reactor is a trickle bed reactor.

11. The process according to claim 1, wherein the reaction is carried out at a temperature in the range from ≥120° C. to ≤250° C.

12. The process according to claim 1, wherein the reaction is carried out in the presence of a solvent having ether or alcohol groups.

* * * * *